United States Patent [19]
Yvin et al.

[11] Patent Number: 5,980,916
[45] Date of Patent: Nov. 9, 1999

[54] USE OF LAMINARIN AND OLIGOSACCHARIDES DERIVED THEREFROM IN COSMETICS AND FOR PREPARING A SKIN TREATMENT DRUG

[75] Inventors: Jean-Claude Yvin; Florence LeVasseur, both of Saint Malo; Fabienne Hud'Homme, Saint Jacut de la Mer, all of France

[73] Assignee: Laboratories Goemar S.A., Saint Malo, France

[21] Appl. No.: 08/737,134

[22] PCT Filed: May 11, 1995

[86] PCT No.: PCT/FR95/00618

§ 371 Date: Nov. 7, 1996

§ 102(e) Date: Nov. 7, 1996

[87] PCT Pub. No.: WO95/31177

PCT Pub. Date: Nov. 23, 1995

[30] Foreign Application Priority Data

May 11, 1994 [FR] France .................................. 94 05795

[51] Int. Cl.⁶ .............................. A61K 7/00; A61K 7/48; C07G 17/00; C07H 1/08
[52] U.S. Cl. .......................... 424/401; 424/418; 536/114; 536/123; 536/123.12
[58] Field of Search .................................... 424/401, 418; 536/114, 123, 123.12

[56] References Cited

U.S. PATENT DOCUMENTS 5,508,033  4/1996  Briand ................................. 424/195.1

FOREIGN PATENT DOCUMENTS 2114989  of 1972  France .
66018360  4/1963  Japan .
2005485  4/1994  Russian Federation ....... A61K 35/80

OTHER PUBLICATIONS

Di–Luzio et al. Journal of the Reticuloendothelial Society 8(5): 465–473, 1970.

Fedorov et al. (A) Chemical Abstracts 116(4) p. 444 Abstract No. 27871, 1992.

Fedorov et al. (B) Chemical Abstracts 116(4) p. 444 Abstract No. 27820, 1992.

Fedorov et al. (C) Chemical Abstracts 116(1) p. 490 Abstract No. 91169, 1992.

*Primary Examiner*—Frank C. Eisenschenk
*Assistant Examiner*—Mary K Zeman
*Attorney, Agent, or Firm*—Dennison, Meserole, Scheiner & Schultz

[57] ABSTRACT

A cosmetic or pharmaceutical, particularly dermatological, composition including an effective amount of laminarin or laminarin-derived oligosaccharides as the active ingredient. It has been discovered that laminarin, oligosaccharides derived therefrom and compositions containing same have stimulating, regenerating, conditioning and energising effects on human dermis fibroblasts and human epidermis keratinocytes. Said composition is useful in cosmetics and pharmacology.

21 Claims, 2 Drawing Sheets

USE OF LAMINARIN AND OLIGOSACCHARIDES DERIVED THEREFROM IN COSMETICS AND FOR PREPARING A SKIN TREATMENT DRUG

BACKGROUND OF THE INVENTION

The present invention relates essentially to the use of laminarin and oligosaccharides derived from laminarin in cosmetology and for the manufacture of a medicine destined for the treatment of the skin.

It is known that laminarin is a storage polymer of brown algae and consists of polysaccharides whose structures differ slightly according to the nature of the alga.

In general terms, laminarin possesses a molecular mass of less than about 30000 Daltons and consists of 20 to 60 D-glucopyranoside units distributed in a main linear chain, in which these units are joined by β(1–3) linkages, and branches joined to this main chain by β(1–6) linkages.

Some of these chains have a reducing terminal unit consisting of a mannitol unit. The existence of mannose units within this structure is also noted.

Laminarin is generally extracted from brown macrophytt marine algae of the Pheophyceae type, and in particular the Fucales or the Laminariales.

Various extraction methods can be used to obtain the laminarin.

Reference may be made for example to the method described by Black et al., Appl. Chem., 1951, 1, pages 505 to 517.

More generally, laminarin can be obtained from brown algae by any extraction process which enables the constituents other than laminarin (wall polysaccharides, salts, etc.) to be successively removed.

In particular, these processes use steps involving grinding, precipitation in an acid or basic medium, ultrafiltration and dialysis.

Laminarin is also marketed, for example by Sigma Chimie SARL.

Various scientific publications describe the eliciting properties of laminarin, suggesting its use for enhancing plant defense reactions.

Thus Netzer et al. reveal that an infection with the pathogen S. oxysporum triggers the induction of laminarinase (Biological abstracts, vol. 68, No. 1, 1979).

Likewise, Bonhoff et al. reveal the properties of laminarin as an elicitor of phytoalexin and callose (Biological abstracts, vol. 86, No. 4, 1988).

Furthermore, Kurosaki et al. (Biological abstracts, vol. 35, No. 2, 1988) and Pearce (Biological abstracts Vol. 74, No. 8, 1982) confirm the eliciting effects of laminarin, in particular in respect of lignification, while at the same time state that these effects are weak compared with those of the known elicitors.

The French Patent Application No. 92 08387 of the Applicants confirm the eliciting properties of laminarin and its use for enhancing plant defense reactions, and further reveal that laminarin has the properties of an α-amylase elicitor causing an accelerating action on seed germination and plant growth.

Furthermore, it is known that sulfated laminarin has interesting pharmaceutical properties, in particular anticoagulant and hypoi-holesterinemiant properties. (K. C. Guven et al., Introduction to Applied Physiology, 1990, pages 67 to 92).

SUMMARY OF THE INVENTION

It was discovered, and this constitutes the basis of the present invention, that laminarin, the oligosaccharides derived from laminarin and the compositions containing them, possess stimulant, regenerating, revitalizing, and energizing effects on the fibroblasts of the human dermis, support tissue of the skin and on the keratinocytes of the human cutaneous epidermis, as well as on target cells of cosmetic or pharmaceutical products, notably dermatological products.

These effects have been demonstrated by the study of the stimulation of the neosynthesis of proteins in cultures of skin cells.

The cell cultures in fact allow the measurement of the Tolerance and the activity of products under test, insofar as where, in appropriate culture conditions, these cells retain functions close to those expressed in vivo.

It seems, without this constituting a theoretical interpretation, that the effects of stimulation obtained are due to the two following mechanisms:

on the one hand, laminarin, the oligosaccharides derived from laminarin, and the compositions containing them, would have a nutritious effect and would provide cells with elements absent or present in an insufficient quantity in the culture medium;

on the other hand, these products would have an effect similar to those of a hormone (<<hormone-like >>), i.e. that they would transmit to the cells signals which would modify the activity of the latter.

It has been noted that the effects of stimulation of laminarin, oligosaccharides derived from laminarin and compositions (containing them, manifest themselves at low concentrations, compatible with those which can be used in a cosmetic or pharmaceutical composition.

Thus, according to a first aspect, the present application aims to cover the use in cosmetology of laminarin and oligosaccharides derived from laminarin as a stimulant, a regenerating or revitalizing agent and with energizing activity on the fibroblasts and the keratinocytes.

The expression <<oligosaccharides derived from laminarin >> used in the present description and claims, indicates any product susceptible of being obtained from laminarin by a process comprising its chemical or enzymatic hydrolysis.

The chemical hydrolysis is generally carried out by the action of an acid such as, for example, 0.1 M sulfuric acid on the laminarin at a temperature ranging from 50° C. to 100° C. and preferably a temperature of about 80° C., for a period of time ranging from 3 hours to 8 hours, preferably 6 hours.

This hydrolysis is optionally followed by a neutralization by the addition of a strong base until a pH ranging from 6 to 8 is obtained, and then a desalting step carried out by passing the product thus neutralized through. an ion exchange resin and optionally followed by a reduction step in the form of a powder by lyophilization or atomization.

The enzymatic hydrolysis is generally carried out b y the action, on laminarin, of an enzyme of the type Endo β-glucanase such as laminarinase which may be of animal, vegetable, bacterial or fungal origin.

The parameters of the hydrolysis (pH, temperature, duration, concentrations of the substrate and the enzyme) can be easily determined by the person skilled in the art according to the optimal conditions of the activity of the enzyme.

After the inactivation of the enzyme, which can be carried out at 100° C. for 10 minutes, the product obtained can eventually be submitted to a tangential ultrafiltration of 50000 Daltons, and then a desalting step on an ion exchange resin and can optionally be submitted to a reduction in the form of a powder by lyophilization or atomization.

Generally, laminarin and the oligosaccharides derived from laminarin used as a stimulant, a regenerating or revitalizing agent and with energizing activity on the fibroblasts and the keratinocytes in the framework of the present invention, allow the manufacture of cosmetic compositions.

According to a particular characteristic, this cosmetic composition contains, expressed in percentage by weight, from 0.00001% to 10% of laminarin or oligosaccharides derived from laminarin.

Advantageously, this quantity is in the range 0.1% to 5%.

Such a cosmetic composition can be presented in the form of an aqueous solution, a simple or multiple emulsion, or even in the form of a solid, notably a powder, a tablet or a gelatin capsule.

These compositions are prepared according to methods normally used in the cosmetic or pharmaceutical domains.

For example, laminarin or the oligosaccharides derived from laminarin can be dissolved in an aqueous phase for the preparation of an aqueous solution.

This solution can eventually allow an emulsion to be obtained by mixing it with different components such as a tensioactive or an emulsifying agent, an oil or a fatty acid, a fatty alcohol, a wax, a gelling agent, a moisturizing agent, glycerine or a glycol.

Optionally, these compositions may further contain an additional substance selected from preservatives and perfumes.

According to a second aspect, the present application aims to cover the use of laminarin or oligosaccharides derived from laminarin for the manufacture of a medicine destined for the treatment of the skin.

According to a particular characteristic, this medicine is presented in the form of a solid, in particular a powder, a tablet, a gelatin capsule or a drinkable syrup, or a cream for topical application.

These pharmaceutical forms are prepared according to normal methods.

The active ingredient constituted by a pharmaceutically effective amount of laminarin or oligosaccharides derived from laminarin, is incorporated with excipients normally employed in these pharmaceutical compositions, such as talc, gum arabic, lactose, starch, magnesium stearate, polyvidone, cellulose derivatives, a fatty embodiment of animal or vegetal origin, and various wetting agents, dispersing agents or emulsifiers as well as preservatives, flavors and colorants.

In a third aspect, the present application aims to cove-r a cosmetic or pharmaceutical composition, notably a dermatological composition, characterized in that it contains, as active ingredient, an effective quantity of oligosaccharides derived from laminarin, in association with a cosmetically or pharmaceutically acceptable carrier or vehicle.

According to a particular characteristic, this cosmetic composition, expressed as percentage by weight, contains, from 0.00001% to 10% of oligosaccharides derived from laminarin.

Advantageously, this quantity is in the range 0.1% and 5%, by weight.

Such a cosmetic composition can be presented in the form of an aqueous solution, a simple or multiple emulsion, or even in the form of a solid, notably a powder, a tablet or a gelatin capsule.

This composition can be prepared according to the methods normally used in the cosmetic or pharmaceutical domains that are given above.

DESCRIPTION OF THE PREFERRED EMBODIMENTS

The present invention will be illustrated in greater detail with the aid of the following non-limiting examples.

Laminarin can be extracted in accordance with the process mentioned in the French Patent Application No. 92.08387, incorporated here by way of reference. Examples 1 and 2 hereinafter illustrate other processes for obtaining laminarin or oligosaccharides derived from laminarin.

EXAMPLE 1

Process for the Extraction of Laminarin from a Brown Alga.

105 g of dry algae of type Laminaria digitata are submitted to an extraction by 1.5 l of 0.09 M sulfuric acid.

The extraction is effected in a water-bath at a temperature of about 70° C. for 2 hours 30 minutes.

The extract is filtered under vacuum on a Whatman GF/A filter, then on a 0.45 μm Millipore filter.

The liquid thus obtained is submitted to a tangential ultraliltration at 5000 Daltons. For this, a Pellicon system, marketed by Millipore, equipped with a cassette of 5000 Dalton porosity is used in association with a Procon pump, also marketed by Millipore.

The operation is effected in maintaining a pressure of 3 bars on the filtration cassette.

A filtrate of about 1.3 litres of pH 3 to 5 is thus obtained, which is then submitted to a lyophilization leading to 5.5 g of dry powder corresponding to 90% pure laminarin.

EXAMPLE 2

Process for the Preparation of Oligosaccharides Derived from Laminarin.

10 g of laminarin extracted according to Example 1 are submitted to the action of 1 g of a β(1–3) glucanase (laminarinase). The enzymatic reaction is carried out in 1 l of 0.05 M acetate buffer (pH 5) medium.

This mixture is incubated at 37° C. for 20 minutes. Then in inactivation of the enzyme is effected in a water bath at 100° C. for 10 minutes. After cooling to room temperature, the product is submitted to a tangential ultrafiltration of 50000 Daltons in such a way as to remove the inactivated enzyme.

This is carried out on a carbon-ceramic tubular membrane of the <<Carbosep>> type of 50000 Daltons porosity.

The operation is carried out in maintaining a pressure of 1 bar on the filtration column. A filtrate of a volume of about 0.9 litres is thus obtained, of pH 5 and of a resistivity of 175 Ohms/cm.

This is then submitted to a desalting step. In this, it is treated on a cation exchange column of the type strong exchanger such as Amberlite IR 120® then, on an anion exchange resin of the type strong exchanger such as Amberlite IRA 400®.

A product presenting a resistivity of 2000 Ohms/cm is thus obtained, of volume 0.9 l. After atomization, 3.6 g of oligosaccharides derived from laminarin are thus obtained.

Laminarin and the oligosaccharides derived from laminarin obtained in Examples 1 and 2 were submitted to a high performance liquid chromatography.

Figure 1:
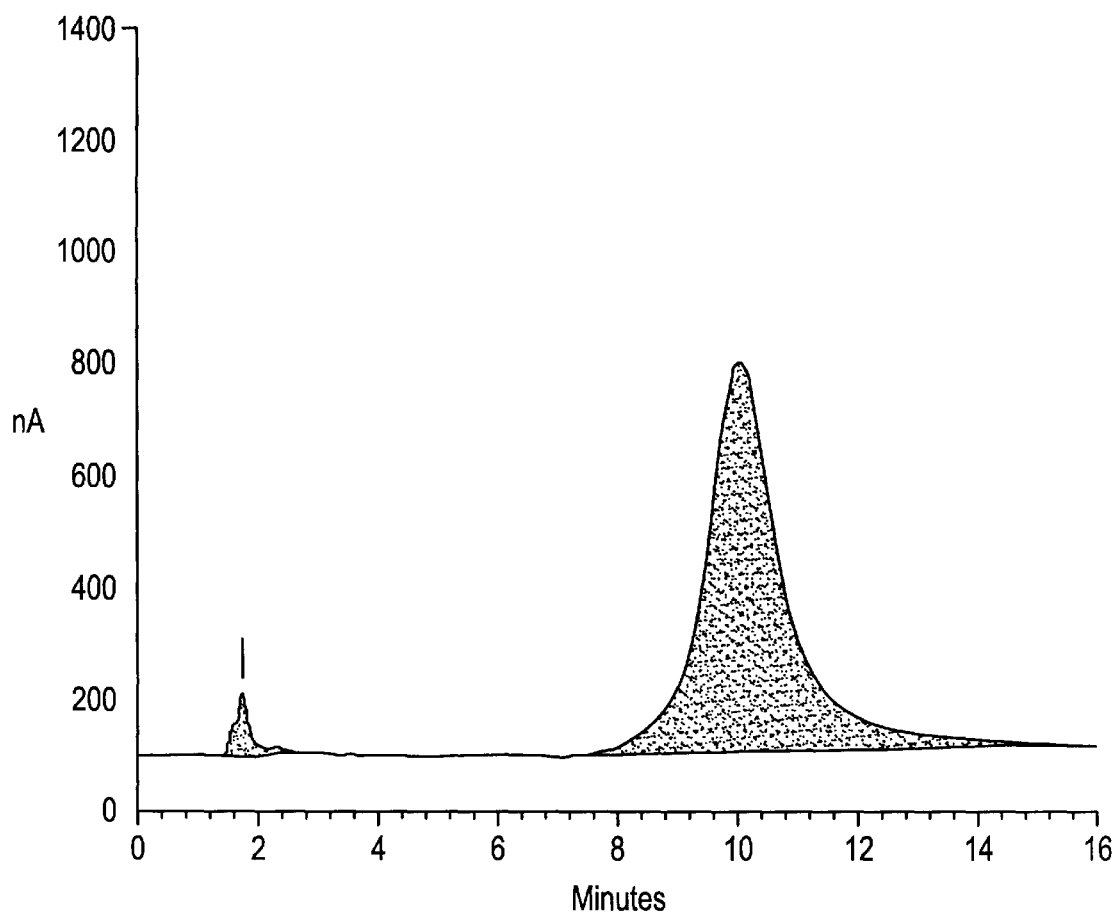
FIG. 1 is an HPLC spectrum for larninarin.
Figure 2:
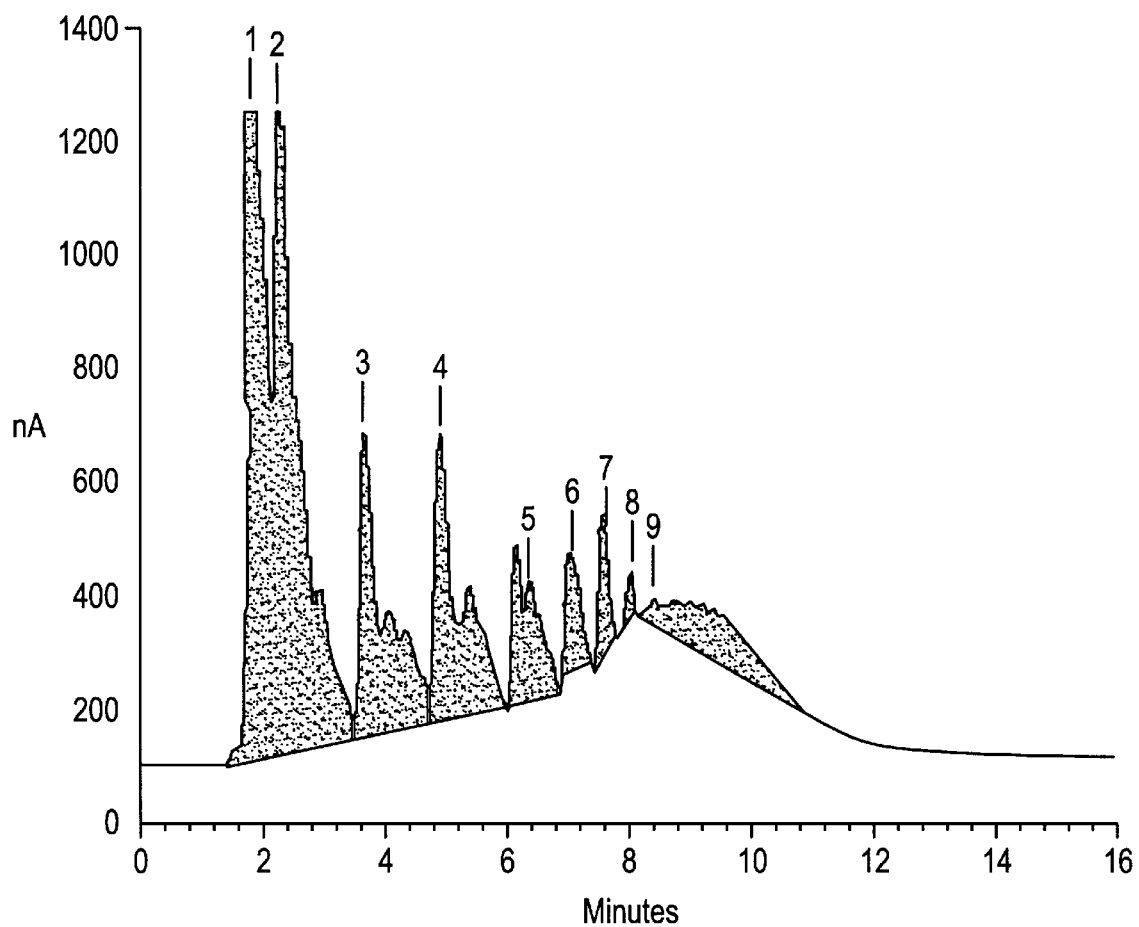
FIG. 2 is an HPLC spectrum for oligosaccharide hydrolysis products of laminarin.

The HPLC spectra are given respectively in FIGS. 1 and 2.

It is specifically noted that these spectra were obtained with an injection of 50 μl using a DIONEX® chromatograph and with an ammeter as the detector.

EXAMPLE 3

The properties of the compounds in accordance with the present invention were demonstrated by carrying out the experiments described below.

EXPERIMENT No. 1

Demonstration of the Stimulant Properties of Laminarin in Cultures of Fibroblasts of Human Dermis.

The effect of laminarin obtained according to Example 1 was studied in cultures of fibroblasts from human dermis. The activity of laminarin was evaluated after 20 hours of incubation by the measurement of a functional parameter, the incorporation of $^{14}C$ radiolabelled Leucine in the proteins, which reflects the neosynthesis of the proteins.

The fibroblasts were isolated from samples of the skin effected during mammary plastic surgery on women aged 44 years old. These fibroblasts were obtained after dissociation of the epidermis and the dermis by trypsin.

The reference cultures were effected in parallel, in the absence of laminarin:

either in the <<reference culture>>:
  CMAF: culture medium for the incubation of fibroblasts in the presence of minimum essential medium (MEM) to which is added 100 IU/ml of penicillin and 100μg/ml of streptomycin.

or in the <<positive reference culture>>:
  CMAF: culture medium for the attachment of the fibroblasts: MEM/M199 (name given to a medium of standard culture) in the proportions ¾:¼ (v/v) to which is added 100 IU/ml of penicillin, 100 μg/ml of streptomycin and 10% (v/v) of foetal calf serum (FCS).

The complete medium (positive reference) gives rise to an enhancement in the incorporation of the leucine in the proteins of the fibroblasts by a factor equal to 1.7.

This value is within the range of cells normally obtained in the laboratory; it demonstrates the capacity of the cells to respond to stimulant factors.

Laminarin obtained according to Example 1 was introduced into proliferating fibroblasts for 20 hours.

The fibroblasts were incubated with $^{14}C$ radiolabelled leucine ($^{14}C$ radiolabelling on carbon 1, specific activity 1.92 GBq/mmole) for 4 hours. The culture medium used for the incorporation of $^{14}C$ leucine in the proteins is the leucine-free MEM medium to which is added 100 IU/ml of pericillin, 100 μg/ml of streptomycin and $9.6 \times 10^{-6}$ M of radiolabelled leucine (18.5 kBq/ml). The cellular mats were washed in order to remove the non-incorporaited precursor and were then counted by liquid scintillation. The values are expressed in dpm/culture well.

Laminarin is directly dissolved in the incubation medium at doses of 0.1, 1, 10, 100 and 1000 μg/ml. Each assay is repeated 4 times.

The results obtained are given in the following Table:

| | Reference without laminarin | LAMINARIN in μg/ml | | | | |
|---|---|---|---|---|---|---|
| | | 0.1 | 1 | 10 | 100 | 1000 |
| Assay 1 | 818 | 872 | 877 | 1015 | 979 | 978 |
| Assay 2 | 761 | 801 | 976 | 1188 | 1108 | 1070 |
| Assay 3 | 739 | 848 | 926 | 973 | 980 | 974 |
| Assay 4 | 769 | 875 | 888 | 1070 | 932 | 1053 |

-continued

| | Reference without laminarin | LAMINARIN in μg/ml | | | | |
|---|---|---|---|---|---|---|
| | | 0.1 | 1 | 10 | 100 | 1000 |
| Average | 772 | 849 | 917 | 1062 | 1000 | 1019 |
| ± deviation | ± 33 | ± 34 | ± 45 | ± 93 | ± 76 | ± 50 |
| % with respect to reference | 100 | 110 | 119 | 138 | 130 | 132 |

Laminarin has, under the tested experimental conditions, an optimal activity at the concentration of 10 μg/ml.

Laminarin enhances the neosynthesis of the proteins in the fibroblasts, by a factor of 1.3, at concentrations ranging from 10 to 1000 μg/ml, in a culture medium totally devoid of foetal calf serum, which demonstrates the stimulant effect of laminarin.

EXPERIMENT No. 2

Demonstration of the Stimulant Properties of Laminarin in Cultures of Keratinocytes of the Human Epidermis.

The effect of the laminarin obtained according to Example 1 was studied in cultures of keratinocytes of the human epidermis.

Its activity was evaluated after 20 hours of incubation by the measurement of a functional parameter, the incorporation of $^{14}C$ radiolabelled leucine in the proteins, which reflects the neosynthesis of the proteins.

The keratinocytes were isolated from samples of skin during mammary plastic surgery on women aged 34 years old. These keratinocytes were obtained after dissociation of the epidermis and the dermis by trypsin, they were cultivated with fibroblasts of mouse embryos (3T3) whose capacity to divide was blocked by mitomycin C (Green's Model).

Reference cultures were effected in parallel, in the absence of laminarin:

either in the <<reference culture>> medium (CMIK) culture medium for the incubation of the keratinocytes in the presence of CMAK compounds, medium with neither epidermal growth factor EGF nor foetal calf serumr FCS, diluted to ¹/₁₀ e in MEM medium (minimum essential medium), to which is added 100 IU/ml of penicillin and 100 μg/ml of streptomycin.

or in the <<positive culture medium>>(CMAK): culture medium for the attachment of keratinocytes i. e. a MEM/M199 medium (name given to a standard culture medium) in the proportions ¾:¼ (v/v) to which is added 100 IU/ml of penicillin, 100 μg/ml of streptomycin, 10% (v/v) of foetal calf serum, 10 ng/ml of epidermal growth factor (EGF), 10 ng/ml of choleraic toxin, 5 μg/ml of bovine insulin, 0.4 μg/ml of hydrocortisone, 5 μg/ml of choline and 8.5 μg/ml of inositol.

Laminarin was placed in the presence of the proliferating keratinocytes for 20 hours.

The keratinocytes were incubated with the $^{14}C$ radiolabeled leucine for 4 hours. The culture medium used for the incorporation of $^{14}C$ leucine in the proteins is the leucine-free MEM medium to which is added 100 IU/ml of penicillin, 100 μg/ml of streptomycin and $9.6 \times 10^{-6}$ M of radiolabelled leucine (18.5 kBq/ml).

The cellular mats were washed in order to remove the rnon incorporated precursor and were then counted by liquid scintillation. The values are expressed in dpm/culture well.

Laminarin is directly dissolved in the incubation medium at doses of 0.1, 1, 10, 100, 1000 μg/ml. Each assay is repeated 4 times.

The results obtained are shown in the following Table:

|  | Reference without laminarin | LAMINARIN in µg/ml | | | | |
| --- | --- | --- | --- | --- | --- | --- |
|  |  | 0.1 | 1 | 10 | 100 | 1000 |
| Assay 1 | 5862 | 6033 | 6522 | 7462 | 7693 | 6264 |
| Assay 2 | 5642 | 6733 | 7178 | 8159 | 8778 | 7723 |
| Assay 3 | 5642 | 5869 | 7449 | 9909 | 7713 | 7386 |
| Assay 4 | 5375 | 4966 | 5648 | 8241 | 7073 | 7811 |
| Average | 5630 | 5900 | 6699 | 8443 | 7814 | 7296 |
| ± deviation | ± 199 | ± 727 | ± 802 | ± 1038 | ± 708 | ± 712 |
| % with respect to reference | 100 | 105 | 119 | 150 | 139 | 130 |

Thus, laminarin enhances the neosynthesis of the proteins in the keratinocytes of the human dermis, by a factor of 1.3 to 1.5, at concentrations ranging from 10 to 1000 µg/ml. It presents, under the experimental conditions tested, an optimal activity at the concentration of 10 µg/ml.

EXPERIMENT No. 3
Demonstration of the Stimulant Proteins of the Oligosaccharides Derived from Laminarin in Cultures of Fibroblasts of the Human Dermis.

In this experiment, the effect studied is that of the oligosaccharides derived from laminarin obtained in Example 2.

The conditions of operation in this experiment are the same as those in Experiment No. 1. The oligosaccharides are directly dissolved in the incubation medium at doses of 0.1, 1, 10, 100, 1000 µg/ml. Each assay is repeated 4 times.

The results are shown in the following Table:

|  | Reference without oligosaccharide | OLIGOSACCHARIDES DERIVED FROM LAMINARIN (µg/ml) | | | | |
| --- | --- | --- | --- | --- | --- | --- |
|  |  | 0.1 | 1 | 10 | 100 | 1000 |
| Assay 1 | 818 | 798 | 861 | 1022 | 1014 | 1059 |
| Assay 2 | 761 | 925 | 947 | 1074 | 1169 | 958 |
| Assay 3 | 739 | 846 | 860 | 1146 | 1184 | 984 |
| Assay 4 | 769 | 806 | 781 | 1163 | 1154 | 1129 |
| Average | 772 | 844 | 862 | 1101 | 1130 | 1032 |
| ± deviation | ± 33 | ± 58 | ± 68 | ± 65 | ± 78 | ± 77 |
| % with respect to reference | 100 | 109 | 112 | 143 | 146 | 134 |

These results show that the oligosaccharides derived from laminarin enhance the neosynthesis of the proteins in the fibroblasts of the human dermis by a factor of 1.4 at concentrations ranging from 10 to 1000 µg/rnl. The maximal effects are observed at 10 and 100 µg/ml.

EXPERIMENT No. 4
Demonstration of the Stimulant Properties of the Oligosaccharides Derived from Laminarin in the Cultures of Keratinocytes of the Human Epidermis.

In this experiment, the effect studied is that of the oligosaccharides derived from laminarin obtained according to Example 2.

The conditions of operation in this experiment are the tame as those of Example No. 2. The oligosaccharides are directly dissolved in the incubation medium at doses of 0.1, 1, 10, 100, 1000 µg/ml. Each assay is repeated 4 times.

The results are shown in the following Table:

|  | Reference without oligosaccharide | OLIGOSACCHARIDES DERIVED FROM LAMINARIN (µg/ml) | | | | |
| --- | --- | --- | --- | --- | --- | --- |
|  |  | 0.1 | 1 | 10 | 100 | 1000 |
| Assay 1 | 5862 | 6652 | 7075 | 8124 | 9028 | 7503 |
| Assay 2 | 5642 | 6551 | 7281 | 8289 | 9314 | 9181 |
| Assay 3 | 5642 | 6701 | 7361 | 8862 | 9483 | 8611 |
| Assay 4 | 5375 | 5627 | 6379 | 9973 | 8634 | 7697 |
| Average | 5630 | 6383 | 7024 | 8812 | 9115 | 8248 |
| ± deviation | ± 199 | ± 508 | ± 447 | ± 836 | ± 371 | ± 788 |
| % with respect to reference | 100 | 113 | 125 | 157 | 162 | 146 |

These results show that the oligosaccharides derived from laminarin enhance the neosynthesis of the proteins in the keratinocytes of the human epidermis by a factor of 1.6 at concentrations ranging from 1 to 1000 µg/ml. The maximal effects are observed at 10 and 100 µg/ml.

Different cosmetic or pharmaceutical compositions containing laminarin or oligosaccharides derived from laminarin such as prepared in Examples 1 and 2 will be given in Examples 4 to 7 below.

EXAMPLE 4

Formulation of a pharmaceutical ointment with healing action in which laminarin is integrated.

| HEALING OINTMENT | |
| --- | --- |
|  | % |
| Paraffin oil | 95.1 |
| Polyethylene sorbitan trioleate (E200) | 2.5 |
| Calendula extract | 1.0 |
| Essential Oil of *Melaleuca alternifolia* | 0.5 |
| Laminarin | 0.5 |
| Preservative | 0.4 |

EXAMPLE 5
Formulation of a Cosmetic Cream with Regenerating Action Containing Laminarin as Active Ingredient.

| REGENERATING CREAM | |
| --- | --- |
|  | % |
| Purified water | 69.4 |
| Isocetyl stearate | 11.0 |
| Extract of algae | 6.0 |
| Cetyl alcohol | 4.0 |
| Glycerol stearate | 3.5 |
| Glycerol stearate polyethylene glycol ether | 3.5 |
| Silicone oil | 1.0 |
| Laminarin | 0.6 |
| Sodium pyrrolidone carboxylate | 0.5 |
| Preservative | 0.3 |
| Perfume | 0.2 |

EXAMPLE 6
Formulation of a Moisturizing Lotion Containing Oligosaccharides Derived from Laminarin as Active Ingredient.

MOISTURIZING LOTION

|  | % |
| --- | --- |
| Water | 89.1 |
| Extract of algae | 8.0 |
| Glycerine | 1.5 |
| Oligosaccharides derived from laminarin prepared according to Example 2 | 1.0 |
| Preservative | 0.3 |
| Perfume | 0.1 |

EXAMPLE 7

Formulation of a Marine Toothpaste Containing Oligosaccharides Derived from Laminarin as Active Ingredient.

MARINE TOOTHPASTE

|  | % |
| --- | --- |
| Water | 47.6 |
| Calcium carbonate | 25.0 |
| Red alga | 12.0 |
| Extract of alga | 10.0 |
| Carrageenan | 2.0 |
| Oligosaccharides of laminarin prepared according to example 2 | 1.0 |
| Silica | 0.8 |
| Sodium lauryl ether sulfate | 0.8 |
| Methylparaben | 0.5 |
| Flavor | 0.3 |

We claim:

1. A process for stimulating skin cells selected from the group consisting of fibroblasts and keratinocytes comprising delivering to said skin cells an active component consisting essentially of laminarin in an amount effective for stimulating said skin cells.

2. A process according to claim 1, wherein the laminarin is delivered in combination with a cosmetically acceptable excipient.

3. A process according to claim 1, wherein the laminarin is delivered at a concentration of 0.00001 to 100% by weight.

4. A process according to claim 3, wherein the laminarin is delivered at a concentration of 0.1 to 50% by weight.

5. A process for treatment of skin comprising applying to the skin a composition containing an active component consisting essentially of laminarin in an amount effective for stimulating fibroblasts and keratinocytes.

6. A process according to claim 5, wherein the laminarin is delivered in a composition containing a pharmaceutically or cosmetically acceptable excipient.

7. A process for the cosmetic treatment of skin by the stimulation of fibroblasts and keratinocytes comprising applying to the skin a composition containing an active component consisting essentially of laminarin in an amount effective for stimulating fibroblasts and keratinocytes.

8. A process according to claim 7, wherein the laminarin is delivered in combination with a cosmetically acceptable excipient.

9. A process according to claim 7, wherein the laminarin is delivered at a concentration of 0.00001 to 10% by weight.

10. A process according to claim 8, wherein the laminarin is delivered at a concentration of 0.1 to 5% by weight.

11. A process for stimulating fibroblasts comprising delivering to said fibroblasts an active component consisting essentially of laminarin in an amount effective for stimulating said fibroblasts.

12. A process for stimulating skin cells selected from the group consisting of fibroblasts and keratinocytes comprising delivering to said skin cells an active component consisting essentially of oligosaccharide products obtained by hydrolysis of laminarin in an amount effective for stimulating said skin cells, said oligosaccharide products being obtained as a reaction product of lamlnarin with β (1–3) glucanase.

13. A process according to claim 12, wherein the products are delivered in combination with a pharmaceutically or cosmetically acceptable excipient.

14. A process according to claim 12, wherein the products are delivered at a concentration of 0.00001 to 10% by weight.

15. A process according to claim 14, wherein the products are delivered at a concentration of 0.1 to 5% by weight.

16. A process for treatment of skin comprising a step of applying to the skin a composition containing an active component consisting essentially of oligosaccharide products obtained by hydrolysis of laminarin in an amount effective for stimulating fibroblasts and keratinocytes, said oligosaccharide products being obtained as a reaction product of laminarin with β (1–3) glucanase.

17. A process for the cosmetic treatment of skin by the stimulation of fibroblasts and keratinocytes comprising applying a composition to the skin containing an active component consisting essentially of oligosaccharide products obtained by hydrolysis of laminarin in an amount effective for stimulating fibroblasts and keratinocytes, said oligosaccharide products being obtained as a reaction product of laminarin with β (1–3) glucanase.

18. A process according to claim 17, wherein the products are delivered in combination with a cosmetically acceptable excipient.

19. A process according to claim 17, wherein the products are delivered at a concentration of 0.00001 to 100% by weight.

20. A process according to claim 19, wherein the products are delivered at a concentration of 0.1 to 50% by weight.

21. A process for stimulating fibroblasts, comprising delivering to said fibroblasts an active component consisting essentially of oligosaccharide products obtained by hydrolysis of laminarin in an amount effective for stimulating said fibroblasts, said oligosaccharide products being obtained as a reaction product of laminarin with β (1–3) glucanase.

* * * * *